United States Patent [19]

Kollonitsch et al.

[11] Patent Number: 4,483,870

[45] Date of Patent: Nov. 20, 1984

[54] α-DIFLUOROMETHYL AMINO ACIDS AND HYPERTENSION TREATING COMPOSITIONS THEREOF

[75] Inventors: Janos Kollonitsch, Westfield; Stephen Marburg, Metuchen; Arthur A. Patchett, Westfield, all of N.J.

[73] Assignee: Merck & Co., Inc., Rahway, N.J.

[21] Appl. No.: 70,564

[22] Filed: Aug. 29, 1980

Related U.S. Application Data

[63] Continuation of Ser. No. 927,210, Jul. 24, 1978, abandoned.

[51] Int. Cl.[3] .................. A61K 31/24; A61K 31/195;
 C07C 101/32; C07C 101/72
[52] U.S. Cl. .................................... 424/309; 424/319;
 560/40; 562/445
[58] Field of Search .......................... 560/40; 562/445;
 424/309, 319

[56] References Cited

U.S. PATENT DOCUMENTS

| | | | |
|---|---|---|---|
| 2,868,818 | 1/1959 | Pfister et al. | 560/40 |
| 3,046,300 | 7/1962 | Sletzinger et al. | 560/40 |
| 3,322,630 | 5/1967 | Porter | 424/330 |
| 3,839,585 | 10/1974 | Lotti et al. | 424/319 |
| 4,065,566 | 12/1977 | Bodor et al. | 560/40 |

FOREIGN PATENT DOCUMENTS 737907  7/1966  Canada .

OTHER PUBLICATIONS

Kollonitsch et al., J. Org. Chem., 40, 3808–3809, (1975).

*Primary Examiner*—Bernard Helfin
*Attorney, Agent, or Firm*—Alice O. Robertson; Michael C. Sudol

[57]  ABSTRACT

Novel α-difluoromethyl tyrosines and esters thereof are disclosed. The novel compounds have useful pharmacological activity.

6 Claims, No Drawings

α-DIFLUOROMETHYL AMINO ACIDS AND HYPERTENSION TREATING COMPOSITIONS THEREOF

This is a continuation of application Ser. No. 927,210, filed July 24, 1978, now abandoned.

BACKGROUND OF THE INVENTION

The present invention is concerned with novel α-fluoromethyl tyrosines and esters thereof.

An unsubstituted α-fluoromethyl-α-amino alkanoic acid, namely 2-fluoromethylalanine, having the formula:

is known [Kollonitsch et al., J. Org. Chem. 40. 3808–9 (1975)]. No specific pharmacological activity for this compound is suggested. This compound (A) is prepared by fluorodehydroxylation of the corresponding 2-hydroxymethylalanine.

α-Methyl-m-tyrosine and α-methyl-p-tyrosine are known (U.S. Pat. No. 2,868,818). Their use in pharmaceutical compositions is described in U.S. Pat. No. 3,322,630, U.S. Pat. No. 3,839,585 and Canadian Pat. No. 737,907. L-α-methyl-p-tyrosine is also used to treat hypertension in pheochromocytoma.

α-Trifluoromethyl tyrosines are described in U.S. Pat. No. 3,046,300. These compounds deplete norepinephrine in the heart.

α-Difluoromethyl tyrosines and esters having pharmaceutical activity have been discovered.

SUMMARY OF THE INVENTION

α-Difluoromethyl tyrosines and esters thereof.

DESCRIPTION OF THE PREFERRED EMBODIMENTS

An embodiment of the present invention is compounds having the formula

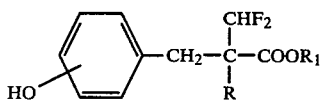

where R is —NH$_2$ and R$_1$ is H or C$_1$–C$_{10}$alkyl.

The pharmaceutically acceptable acid addition salts of the formula I compounds are also included. In general, the salts are those of the formula I base with a suitable organic or inorganic acid. Preferred inorganic acid salts are the hydrohalides e.g. hydrochlorides, hydroiodides, hydrobromides; the sulfates, and the phosphates. The hydrohalides, and especially the hydrochlorides, are more preferred.

The formula I compounds have a chiral center and may occur in optically active forms i.e., as optical isomers. These isomers are designated conventionally by the symbols L and D, + and −, l and d, S and R or combinations thereof. Where the compound name or formula has no isomer designation, the name or formula includes the individual isomer mixtures thereof and racemates.

The compounds having the S-isomer configuration are, in general, preferred.

R$_1$ is H or C$_1$–C$_{18}$alkyl. Examples of suitable alkyl groups are methyl, octadecyl, 2-ethylhexyl, t-butyl, hexyl, isopropyl, ethyl, undecyl and the like; C$_1$–C$_6$alkyl is preferred and ethyl is especially preferred. H is a most preferred definition of R$_1$.

Preferred formula I compounds are those where OH is in the 3 or 4 position with the 4 position being more preferred. Preferred Formula III esters have R, as C$_1$–C$_6$alkyl, especially ethyl. R is H in the more preferred Formula III compounds. Especially preferred Formula III compounds are α-difluoromethyl-m-tyrosine and α-difluoromethyl-p-tyrosine. α-Difluoromethyl-p-tyrosine is most preferred.

The compounds of the present invention have antihypertensive activity. This activity is determined, in vivo, by observing the effect of a compound on blood pressure in a spontaneously hypertensive rat. A representative compound of Formula I was administered intraperitoneally to an (SH) rat and was found to have antihypertensive activity. The compound was also found to have enhanced antihypertensive activity when administered to an (SH) rat which had been pre-treated with the decarboxylase inhibitor carbidopa[S-α-hydrazino-α-methyl-β-(3,4-dihydroxyphenyl)-propionic acid monohydrate].

The observed antihypertensive effect indicates that the present compounds are effective as antihypertensive agents when administered orally or parenterally either alone or in combination with a decarboxylase inhibitor in suitable amounts in an appropriate pharmaceutical dosage form to a hypertensive human. Effective daily dosages may be varied. A suitable daily dosage range is from about 100 to about 3000 mg, with 200–2000 mg being preferred and 250–1500 mg being most preferred.

The ratio of carbidopa: Formula I compound in the combination may be varied and can range from about 1:50 to about 25:1, preferably 1:20 to 5:1 and most preferably 1:5 to 2:1. The pharmaceutical dosage forms (tablets, emulsions, solutions, dispersions, capsules, etc.) are prepared using conventional procedures and compounding ingredients.

A process for preparing the compounds of the present invention where R is NH$_2$ is illustrated by the following equations:

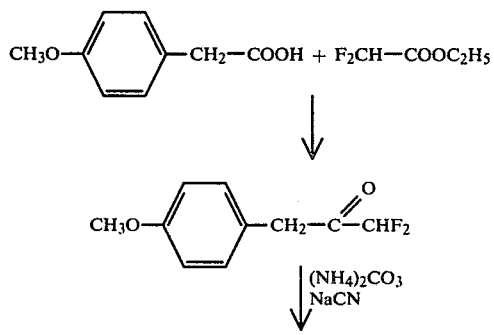

-continued

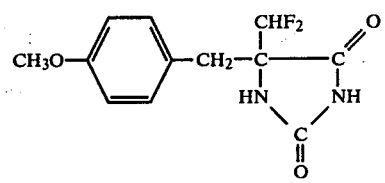

 HCl

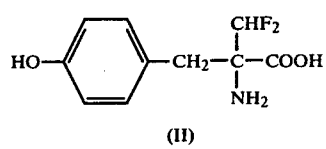

(II)

Esters of II are prepared using conventional esterfication procedures. The following example illustrates the preparation of the Formula II compounds. All temperatures are degrees Celsius.

EXAMPLE I

A. Preparation of p-methoxybenzyl-difluoromethylketone

Twenty-three ml of diisopropylamine (176 mmol) was dissolved in 50 ml of tetrahydrofuran and treated with 66 ml of 2.4M butyllithium (in hexane) over a period of 23 minutes, keeping the temperature between 10°-15° C. by immersion in an ice bath. After cooling the resulting solution of lithium diisopropylamide to −78° C., there was added 13.28 of p-methoxyphenylacetic acid (80 mmol) in 80 ml of tetrahydrofuran over a period of 20 minutes. The temperature was raised to 0° C. and the solution was stirred at this temperature for 3 hours. Then the mixture was recooled to −78° C. and 10.3 g of ethyl difluoroacetate (83 mmol) in 50 ml of tetrahydrofuran was added over 15 minutes keeping the temperature between −78° C. and −60° C. The solution was stirred for 2 hours at this temperature and then quenched onto 800 ml of 2N HCl and the aqueous solution extracted with 4×150 ml ethyl acetate. This was backwashed with 5% NaHCO3 solution and saturated aqueous sodium chloride. After drying the solution was concentrated to 13.7 g of p-methoxybenzyl difluoromethyl ketone.

B. Preparation of 5-p-methoxybenzyl-5-difluoromethyl-2,4-imidazolidinedione

Two grams of p-methoxybenzyl difluoromethylketone (10 mmol), 4.5 g of ammonium carbonate, 10.1 ml of ethanol and 6.6 ml of H2O were heated under nitrogen for 15 minutes at 55° C. Then 0.53 g sodium cyanide was added and the mixture stirred at 55° C. for 21 hr. The temperature was then raised to 90° for 35 min to volatilize most of the (NH4)2CO3. Acidification with conc HCl affords 2.2 g of crude hydantoin II, mp 161°-162°. Recrystallization from 55 ml of H2O afforded 2.0 g of 5-p-methoxybenzyl-5-difluoromethyl-2,4-imidazolidindione (73%) mp 163.5°-164.5° C.

C. Preparation of α-difluoromethyltyrosine 0.84 g of 5-p-methoxybenzyl-5-difluoromethyl-2,4-imidazolidinedione was heated in a sealed tube with 40 ml of conc HCl for 20 hr at 130° C. After cooling the mixture was filtered and concentrated to 1.0 g of crude product. This was dissolved in a minimal amount of conc HCl and applied to a 35-ml column of Dowex 50×8 H+ form (strong acid ion exchange resin). The column was washed with 350 ml of H2O and then with 2N aqueous ammonia. The effluent was monitored with a Uvicord II recording ultraviolet spectrophotometer and the UV absorbing fractions were concentrated in vacuo to 406 mg of α-difluoromethyltyrosine.

Optical resolution of racemic α-difluoromethyl amino acids of this invention may be performed by standard methods described in the literature for resolution of amino acids, e.g., salt formation of esters formed from the α-difluoromethyl amino acids with optically active acids or alternatively by salt formation with optically active bases of N-acylated derivatives of the α-difluoromethyl amino acids, e.g., N-acetyl or N-benzoyl derivatives thereof. Another method of optical resolution consists of separation by elution chromatography of the diastereoisomeric amides obtained by N-acylation of the α-difluoromethyl amino acids by an optically active acid, e.g., by (+)-α-methyoxy-α-trifluoromethylphenylacetic acid. The separated diasteroisomeric acyl amino acids on acid hydrolysis give (S) and (R) isomers of α-difluoromethyl amino acids.

Claims to the invention follow.
What is claimed is:
1. Compounds having the formula

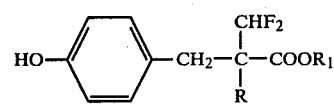

and pharmaceutically acceptable salts thereof wherein
R is —NH2 and
R1 is H or C1–C18alkyl.
2. Compounds of claim 1 wherein R1 is C1–C16alkyl.
3. Compounds of claim 1 wherein R1 is H.
4. The S-isomer of the claim 1 compounds.
5. A pharmaceutical composition for treating hypertension containing an effective amount of a compound of claim 1.
6. The composition of claim 5 wherein R1 is H.

* * * * *